United States Patent [19]

Johnson

[11] Patent Number: 5,545,285

[45] Date of Patent: Aug. 13, 1996

[54] WAIST ELASTIC APPLICATOR FOR DIAPER OR SIMILAR ARTICLE

[76] Inventor: Nordahl K. Johnson, 13812-112th Ave. Ct. East, Puyallup, Wash. 98374

[21] Appl. No.: 341,304

[22] Filed: Nov. 16, 1994

Related U.S. Application Data

[63] Continuation of Ser. No. 41,889, Apr. 2, 1993, abandoned, which is a continuation of Ser. No. 164,752, Mar. 7, 1988, abandoned.

[51] Int. Cl.⁶ ........................................... B32B 31/00
[52] U.S. Cl. ........................... 156/496; 156/439; 156/494; 156/552; 156/568; 156/164
[58] Field of Search ......................... 156/161, 163, 156/164, 229, 265, 303, 494, 495, 496, 519, 552, 568, 434, 439, 177, 179; 26/88, 90; 28/102; 81/424.5

[56] References Cited

U.S. PATENT DOCUMENTS

| Re. 13,974 | 8/1915 | Stevens | 156/439 |
|---|---|---|---|
| 30,801 | 12/1860 | Cleveland | 26/90 |
| 1,238,742 | 9/1917 | Butler | 26/88 |
| 1,949,452 | 3/1934 | Chadwick | 81/424.5 X |
| 2,692,635 | 10/1954 | Polley | 156/439 |
| 2,702,406 | 2/1955 | Reed | 26/88 X |
| 3,728,191 | 4/1973 | Wierzba et al. | 156/519 X |
| 3,805,341 | 4/1974 | Jense | 156/439 X |
| 4,284,454 | 8/1981 | Joa | 156/229 X |
| 4,364,787 | 12/1982 | Radzins | 156/164 |
| 4,642,150 | 2/1987 | Stemmler | 156/164 |
| 4,735,673 | 4/1988 | Piron | 156/164 X |
| 4,925,520 | 5/1990 | Beaudoin et al. | 156/494 |

OTHER PUBLICATIONS

IBM Technical Disclosure, "Self–Centering Non–Contact Pick–up" vol. 22 No. 8A, Jan. 1980.
Webster's II New Riverside University Dictionary, 1984.

*Primary Examiner*—David A. Simmons
*Assistant Examiner*—Paul M. Rivard
*Attorney, Agent, or Firm*—Klarquist, Sparkman Campbell, Leigh and Whinston

[57] ABSTRACT

The disclosure describes an apparatus and method for applying strips of tensioned elastic material transversely to a moving sheet or web of material, such as a component of a disposal diaper. The heart of the invention is a pair of inclinded, spaced apart transfer wheels located in mirror image relationship across the moving web. The transfer wheels are inclined relative to each other so that the distance between them is greatest at a point on their circumference that lies adjacent the web and least where a point on their circumference is at the greatest distance from the web. A supply drum provides an untensioned elastic strip to the transfer wheels at the point of least distance between them. As the transfer wheels move through 180° of rotation, the elastic is stretched and then released at the plane of the web where it is adhesively bonded to the web. A drive system for the transfer wheels rotates them at a circumferential speed essentially equal to the linear speed of the moving web.

8 Claims, 5 Drawing Sheets

WAIST ELASTIC APPLICATOR FOR DIAPER OR SIMILAR ARTICLE

This application is a continuation of application Ser. No. 08/041,889, filed on Apr. 2, 1993, now abandoned, which is a continuation of application Ser. No. 07/164,752, filed Mar. 7, 1988, now abandoned.

BACKGROUND OF THE INVENTION

The present invention relates to a method and apparatus for applying a tensioned elastic member transversely to a moving web of material. More specifically, the apparatus is useful for applying waist zone elastic to a moving assembly in the manufacture of disposable diapers.

Longitudinally positioned elastic in the leg encircling zones of disposable diapers represented a major improvement in the reduction of leakage. A diaper of this type is shown generally in U.S. Pat. No. 3,860,003 to Buell. Machinery for manufacturing the above diaper is described in U.S. Pat. No. 4,081,301 to the same inventor. Subsequent to this time, other inventors in the field have placed elastic in the waist area in order to ensure a more comfortable and leak resistant fit. Examples of diapers of this type are seen in U.S. Patents to Schaar, U.S. Pat. No. 3,951,150; Repke et al, U.S. Pat. No. 4,205,679; Sciaraffa et al, U.S. Pat. No. 4,381,781 and Repke et al, U.S. Pat. No. 4,430,086. The references just cited are intended to be exemplary and not inclusive.

Diapers are normally manufactured in a continuous end-to-end assembly. While the exact manufacturing process will vary somewhat between different manufacturers, most typically preformed absorbent pads of fluffed wood pulp are laid down in a spaced-apart relationship on a continuous sheet of thin polyethylene. These are then covered with a nonwoven fabric which forms the skin contacting surface when in use. Many variations occur in this general procedure including the application of leg elastic, and adhesive attachment tabs in what will become the waist area. One could assume that the application of longitudinally oriented elastic to the moving diaper assembly would be a relatively simple operation. That this is not so is well shown by the considerable number of United States and foreign patents directed to the problem. However, the application of transversely oriented elastic to the waist areas of a continuous assembly moving at high speed represents engineering difficulties of a much greater magnitude. This problem has not yet been solved to the satisfaction of most diaper manufacturers. Reference can be made to Joa, U.S. Pat. No. 4,284,454; Rega, U.S. Pat. No. 4,240,866; Spencer, U.S. Pat. No. 4,523,969; and Van Vliet, U.S. Pat. No. 4,726,874 as examples of machinery for applying transverse elastic. The Spencer patent describes apparatus having a plurality of heads moving orbitally along an elliptical path. These heads are designed to receive and hold two parallel strips of tensioned elastic. As the head is moving at its greatest velocity, at the end of its eliptical path, it contacts the transversely moving diaper assembly and transfers the elastic to the polyolefin backing film. A rotating mechanism attached to each head ensures that they remain oriented with their longitudinal axes always parallel as they travel around a central drive unit. The path of travel is controlled by a cam and follower mechanism which increases the radius of travel in the application zone.

The Van Vliet apparatus has a supporting frame with a shaft providing an axis of rotation for at least one rotatable radial arm. A polygonal head is mounted at the end of each arm. This has a number of peripheral edges with clamps or vacuum orifices for holding a tensioned strand or strands of elastic ribbon. A drive rotates the radial arm and a rotating mechanism moves the heads $(360/n)°$ for each full rotation of the radial arm, where $n$ is equal to the number of peripheral faces on the head. An anvil acts against the head at the time of application of the tensioned elastic to the moving web. The web is passed between the head and the anvil along a path describing a chord or tangent of the circle of rotation of the radial arms.

Young et al, in U.S. Pat. No. 4,726,807 describe another system for making a diaper with an elasticized waistband. This uses as an insert portion of a material which is relatively inelastic as supplied but which becomes elastic upon heating. Alternatively, the entire moisture impermeable backing sheet may be made of the material.

The above-noted examples of machinery for applying transversely oriented elastic to a diaper assembly have been not entirely satisfactory for a number of reasons. In an effort to develop a superior system, the present inventor has searched other fields where a transversely moving first component is applied to a second component moving at right angles. In the field of bag making, U.S. Pat. Nos. 4,289,567 and 4,279,686 to Achelpohl might be noted. However, in this case the machinery operates in intermittent fashion with the second element being stopped during the period when the transversely moving first element is applied. This situation is similar to that shown by Wilson in U.S. Pat. No. 4,316,756 and 4,357,197 where pocket blanks are being applied in intermittent fashion to a moving garment portion. Urban et al, in U.S. Pat. No. 4,135,343 shows a similar intermittent operation where film is being enclosed within a paper mount to form photographic slides. Intermittent operation is also found in U.S. Pat. No. 2,601,005 to Rainey in apparatus to mount lead wires to a capacitor laminate and in U.S. Pat. No. 3,960,641 to Pedersen where handle reinforcements are being placed on carrier bags. In the case of the latter inventor, opposed hexagonal rotary heads carry reinforcement labels which are applied to a moving strip of bag stock. At a second operation remote from this one, elongated hand holds are punched.

Truly continuous operation has been achieved in the diaper industry in the application of waistband adhesive attachment tapes. Examples of equipment to accomplish this function are shown in Wierzba et al, U.S. Pat. No. 3,728,191 and Babcock, U.S. Pat. No. 3,897,293. Endres, in U.S. Pat. No. 3,520,303, shows application of a barrier strip overlying the ends of an absorbent diaper pad. This represents a different and much simpler problem than that of applying a tensioned elastic article. In the latter case the elastic must generally be held in tension while it is bonded to the backing sheet or one of the other diaper components. This requirement greatly complicates the design of suitable machinery.

SUMMARY OF THE INVENTION

The present invention is an apparatus for applying tensioned elastic transversely to a moving web of material. The apparatus is suitable for application of the elastic at high line speeds without interruption or intermittent operation of the moving web. It is especially well adapted for the application of waist zone elastic-to disposable diapers or similar products.

A first essential element of the invention is a pair of spaced apart elastic transfer wheels. These are located in a mirror image relationship transversely across the moving web to which the elastic is to be applied. The transfer wheels each lie in planes which, when projected onto the plane of the web, describe lines parallel to the longitudinal axis of the web. The centers of the transfer wheels are located so that the circumferential edges at one point are adjacent to and essentially tangent to the plane of the web.

The two transfer wheels are inclined relative to each other so that the distance between them is greatest where a point on their circumference lies adjacent the web and least where a point on their circumference is at the greatest distance from the web.

An elastic supply system provides an untensioned elastic strip to the transfer wheels at or adjacent to the point of least distance between them. Each transfer wheel has an elastic retainer which grips the elastic at the point of application, holds it in place during about 180° rotation of the transfer wheels, and then releases it at the plane of the web. A drive system rotates the transfer wheels at a circumferential speed esssentially equal to the linear speed of the moving web. The elastic is applied to the transfer wheels at the point where their edges are closest together and released where they are furthest apart and is stretched an amount equal to the ratio of these two distances.

Normally the stretched elastic will be adhesively bonded to the moving web.

The system for supplying the elastic strips to the transfer wheels may be a cylinder or drum which has its longitudinal axis normal to the longitudinal axis of the moving web. The drum is located so as to be in peripheral proximity to the transfer wheels at the point where the distance between them is least. A continuous sheet of elastic material is supplied to the drum and is partially wrapped around the drum. Individual strips are severed from this sheet by a knife roll which acts against the drum. As the drum rotates, the strip is held in position on the drum from the point of severance to the point of closest proximity to the transfer wheels. There it is released from the drum to the transfer wheels. The drum is driven at a speed essentially identical to that of the circumferential speed of the transfer wheels and the linear speed of the moving web.

A preferred form of drum has a relatively thin wall with a foraminous surface so as to include an internal volume. This internal volume is in communication with a vacuum source which holds the severed elastic strips to the surface while they are moved from the point of severance to the transfer wheels.

A number of different methods can be used to hold the elastic strips on the transfer wheels from the point of pickup from the supply drum to the point of delivery to the moving web. Simple cam actuated clamps are one method. A second method would be to make the transfer wheels themselves hollow with a foraminous periphery in similar fashion to the elastic strip supply drum. In this version, the elastic strips would be held to the transfer wheels by vacuum while they are stretched.

Normally the elastic will be adhesively bonded to the moving web. The apparatus will then include an upstream adhesive applicator which will supply adhesive to at least the location where the tensioned elastic strip is to be placed. In one version, an electronic timing device acts in conjunction with the transfer wheels and adhesive applicator. A strip of adhesive can then be applied to the moving web at the precise location where the tensioned elastic strip is to be later applied. Compression rolls of some kind will then normally press the strip firmly against the adhesive to ensure good bonding.

The heart of the invention is the method and apparatus for applying strips of tensioned elastic in which the elastic is stretched by rotation of wheels which are inclined toward each other at the point of elastic pickup and away from each other at the point of elastic transfer to the moving web.

It is an object of the present invention to provide apparatus for applying strips of tensioned elastic material transversely to a moving sheet or web.

It is a further object to provide apparatus as described in which the web of material is moving at relatively high speed in continuous and uninterrupted fashion.

It is another object to provide an apparatus for applying waist zone elastic to disposable diapers or similar products.

It is yet a further object to provide a method for applying a tensioned elastic ribbon transversely to a moving web of material.

These and many other objects will become immediately apparent to those skilled in the art upon reading the following detailed description taken in conjunction with the drawings.

DESCRIPTION OF THE PREFERRED EMBODIMENTS

The operation of the transverse elastic applicator can be best understood by reference to the drawings. A number of versions are possible using the principles of the present invention, of which only two will be exemplified.

Figure 1:
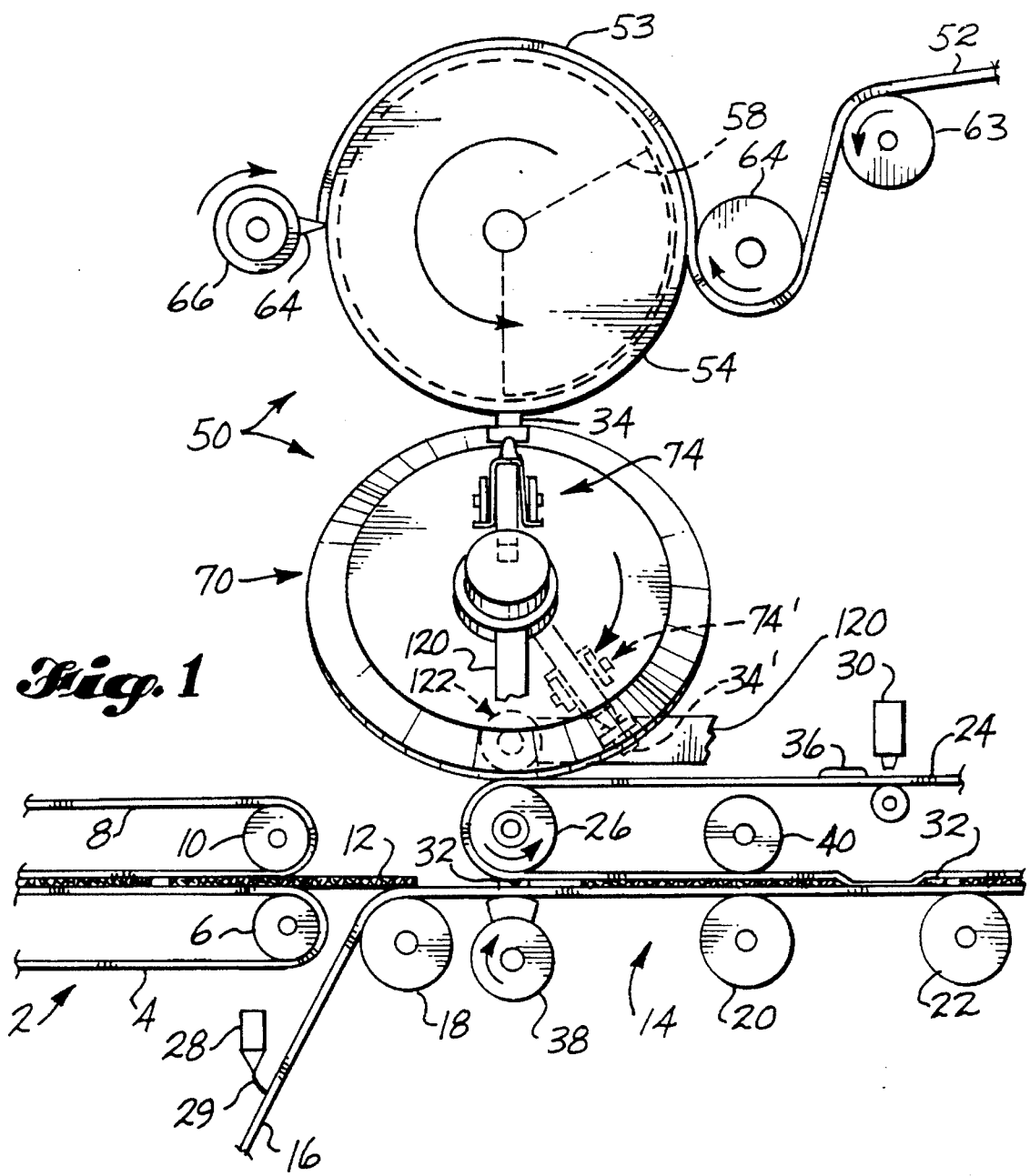
FIG. 1 shows a side elevation view of a portion of a diaper assembly line showing one version of the invention.

FIG. 1 is a fragmentary side elevation of a diaper line at the point where the various components are continuously assembled into complete diaper units. The general method of making disposable diapers is so well known that it need not be elaborated in detail. A pad conveyor unit, generally indicated at 2, brings in absorbent fluff pads 12 on a conveyor line consisting of a driven belt 4, shown here wrapped around a reversing roll 6. An upper assembly comprises a similar belt 8, reeved around a reversing roll 10, which keeps the pads in light compression.

At the diaper assembly section, generally indicated at 14, a thin moisture impervious polyethylene backing sheet 16 continuously moves around support roll 18 where it is thence conducted in a planar configuration over additional support rolls 20 and 22. Polyethylene sheet 16 is moving at a slightly higher speed than that of conveyor 2 so that the individual fluff pads become spaced apart and create pad free waist portions in the individual diaper units. A moisture permeable nonwoven top sheet 24 is fed around reversing roll 26 whereupon it overlays the singulated absorbent pad portions now supported on the polyethylene backing film. An upstream glue applicator 28 places a plurality of parallel fine adhesive lines 29 on the backing film to unite the assembly where combining roll 40 overlies support roll 20. An adhesive applicator 30 is timed with the transverse elastic applicator assembly 50 to apply a plurality of short, parallel fine adhesive lines 36 at appropriate spaced apart distances on the moisture permeable nonwoven sheet 24. The assembly 50 brings down singulated stretched strips of elastic 32 which are applied to nonwoven sheet 24 over fine adhesive lines 36. These are carried around reversing roll 26 and are firmly pressed against the adhesive by a bump roll 38, shown here operating against reversing roll 26. Strips of elastic 34, 34' are shown in positions where they will be applied to the next diaper unit.

It will be understood by those skilled in the art that longitudinal elastic to elasticize the leg areas of the diaper may also be applied. This would be done in well known conventional fashion, normally to the polyethylene backing sheet 16 after the application of the parallel fine adhesive lines by applicator 28.

In the transverse elastic applicator assembly 50, a sheet of untensioned elastic 52 is fed over roll 63 by a driven feed roll 64 onto a vacuum roll 54. A drive means, not shown, for the vacuum roll rotates it counterclockwise. As shown in the embodiment of FIG. 1, after about 180° of travel around roll 54 a synchronized knife roll 66, bearing a cutoff knife 68 operates in conjunction with the vacuum drum 54 carrying sheet 52. The portion of the elastic sheet 53 which lies on the drum is allowed to drag as the drum rotates so that it does not advance as fast as the cutoff strips 34. The feed roll 64 controls the rate at which elastic sheet 52 is advanced onto vacuum roll 54. Feed roll 64 is driven at an appropriate peripheral speed by a drive means, not shown.

Figure 3:
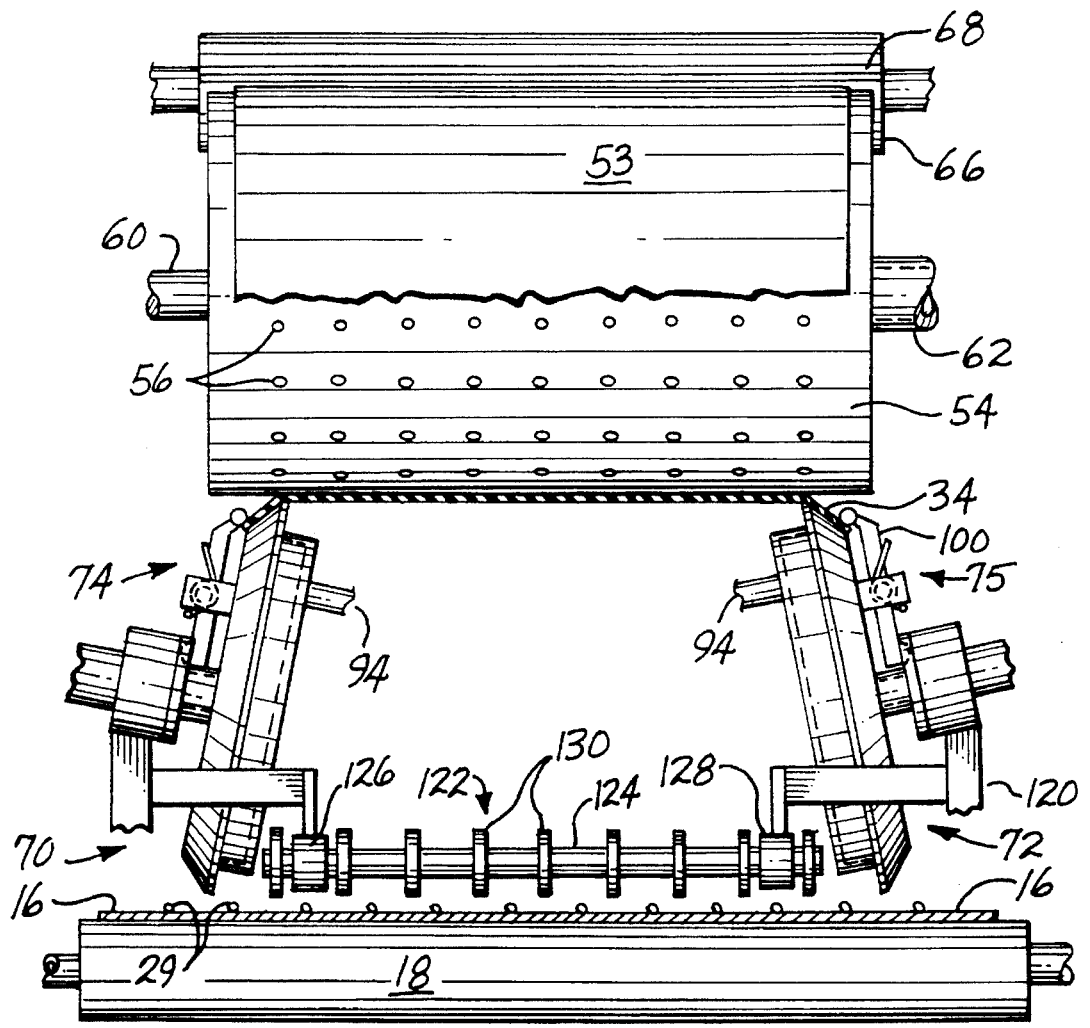
FIGS. 3 and 4 are end elevation views of the embodiment of FIG. 2 taken just downstream from the point of application of the elastic.

Vacuum cylinder or drum 54 may conveniently be supported on a stub shaft 60 and a hollow shaft 62, the latter being in communication with a vacuum pump (FIG. 3). An internal baffle 58 (FIG. 1) controls the portion of the roll to which vacuum will be applied. As shown here, about one third of the roll is blocked off and two thirds are subject to vacuum. Construction of a roll of this type is entirely conventional and does not form a part of the present invention. Those interested in the specifics of construction of a roll of this type might wish to refer to the extensive art on paper machine couch rolls.

Figure 4:
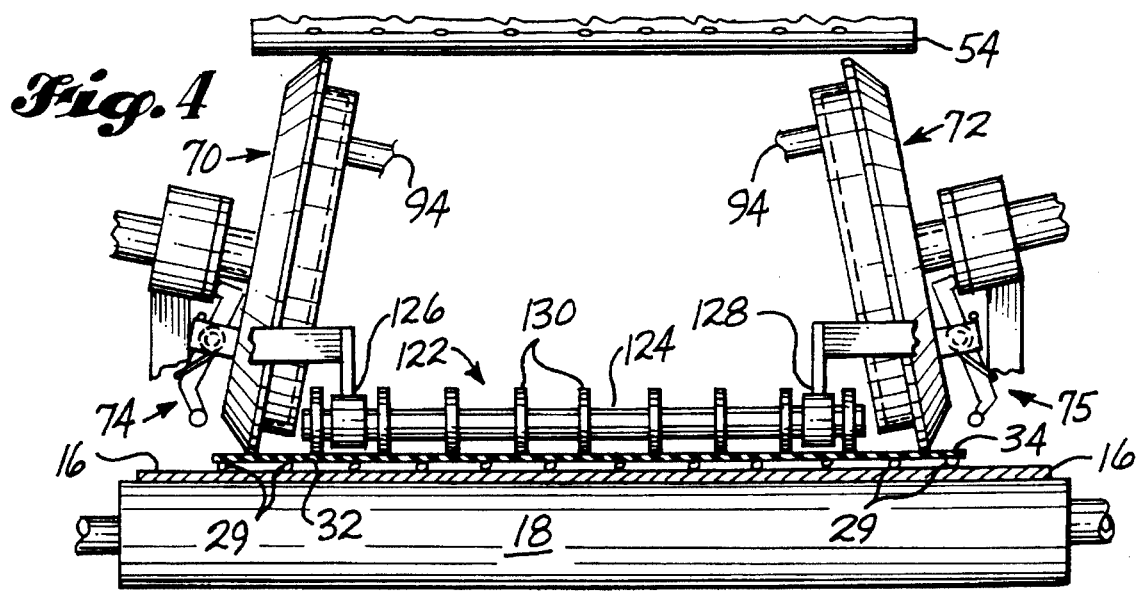

The heart of the invention is found in the use of the inclined elastic transfer wheel assemblies 70, 72, also referred to herein as rotary transfer mechanisms, used to stretch the elastic to the desired degree of tension. FIGS. 3 and 4 best show how these transfer wheels, or mechanisms are arranged. Left inclined elastic transfer wheel assembly or mechanism 70 has an elastic gripper assembly 74 and right inclined transfer wheel assembly or mechanism 72 has an equivalent elastic gripper assembly 75.

Figure 6:
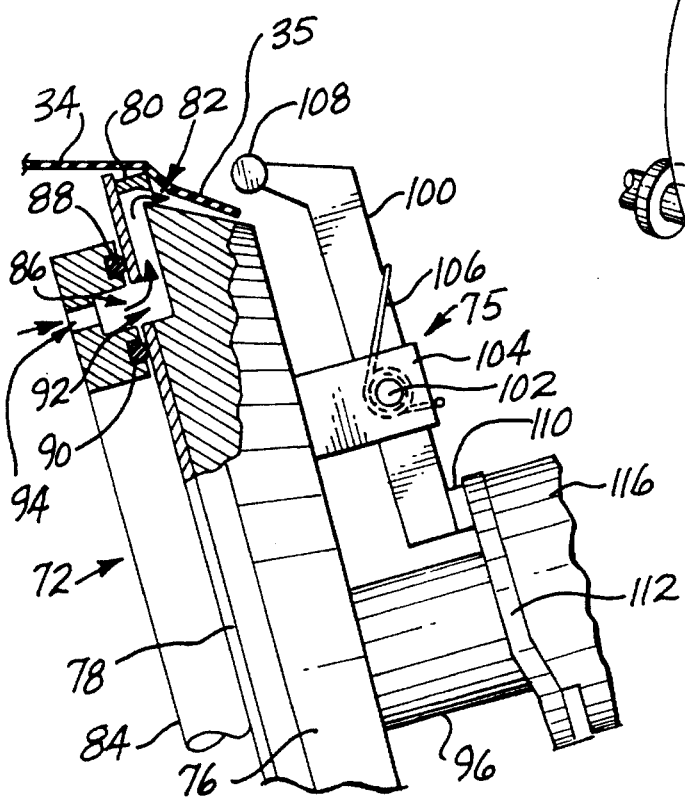
FIG. 6 shows an end elevation, partially in cross section, of the elastic transfer wheel of FIG. 5.
Figure 9:
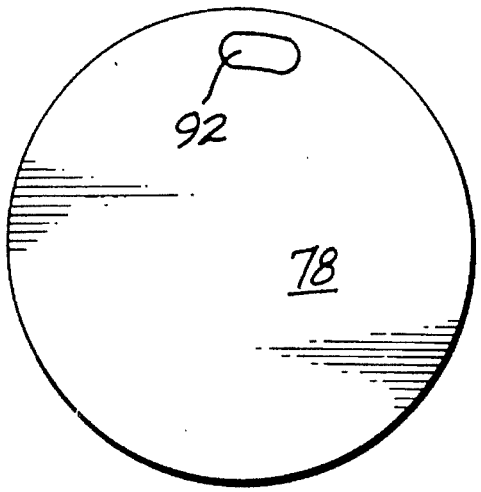
FIG. 9 shows the backing plate of the elastic transfer wheel of FIG. 6.

As is evident from the drawings, each transfer wheel, or mechanism, has a distal, or peripheral, portion spaced outwardly from its axis, adjacent which distal portion the gripper assemblies are mounted. These distal, or peripheral, portions on the opposed wheels are located and rotate with the wheels in mirror image relation between an application point where they are closest together near drum 54 and a release point where they are farthest apart adjacent the plane of the web. The wheels themselves (see FIG. 6) comprise an integral backing plate 78 which in one version will have a lip 80 forming a peripheral nozzle 82. This is attached to frustro-conical portion 76. Portion 76 for each unit has an outer rim surface which slopes toward the center of rotation for the transfer mechanism and away from the other transfer mechanism. A fixed pneumatic ring 84 is in rotary sliding contact with backing plate 78. The pneumatic ring has an inner chamber 86 and is held in tight, leak resistant contact against backing plate 78 by O-ring seals 88, 90. Backing plate 78 has an orifice 92 (see also FIG. 9) which is in register with chamber 86 on pneumatic ring 84 once every revolution. Duct 94 is in communication with a compressed air source which directs a relatively high velocity stream of air along the surface of frustro-conical portion 76 at the location where the transfer wheel assembly is picking up a strip of untensioned elastic 34. The end portion 35 of this elastic strip is drawn down toward the frustro-conical portion 76 of the transfer wheel by Bernoulli effect. At this point it is grasped by the clamping mechanism 75.

Figure 7:
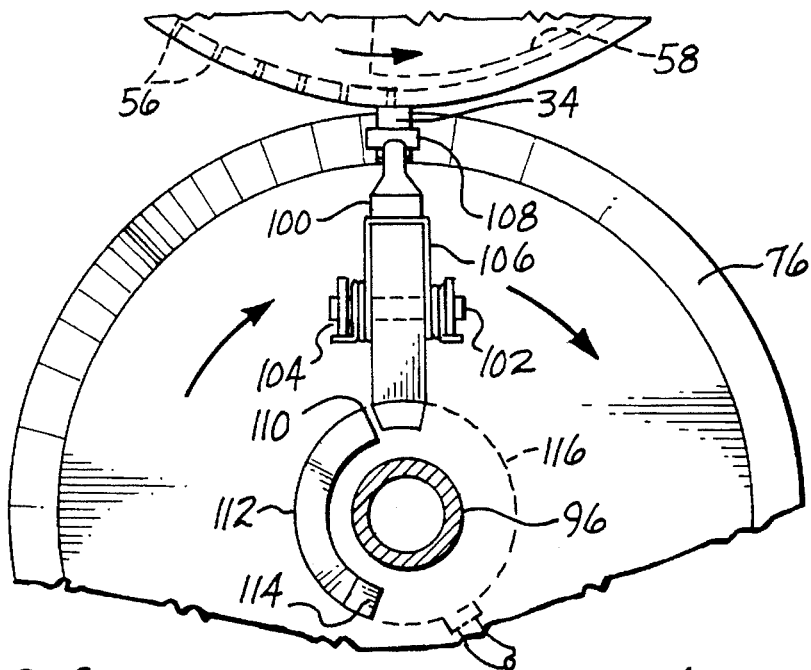
FIG. 7 is a fragmentary side elevation of the elastic transfer wheel of FIG. 5 showing details of the elastic clamp and its operating cam.
Figure 5:
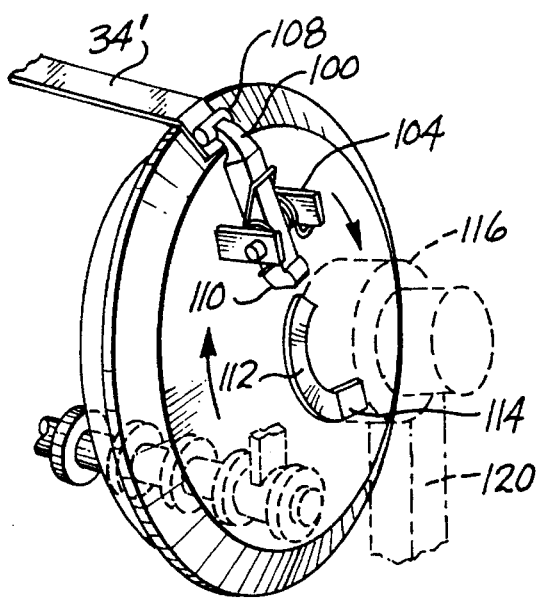
FIG. 5 is a perspective view of one elastic transfer wheel.

The clamping mechanism is identical on both of the elastic transfer wheels. It has an elastic gripper arm 100 pivotally mounted at 102 to bosses 104 upstanding from the frustro-conical portion 76. A biasing spring 106 maintains the gripping end 108 normally in contact with the frustro-conical portion of the transfer wheel. As best seen in FIGS. 3, 4 and 7 the radially inwardly facing gripping portion of the gripping end 108 of the clamping mechanism is spaced radially inwardly from the outer extremity of the wheel. The other end of gripper arm 100 is a cam follower portion 110 which operates against a cam 112 having a raised end 114 (refer to FIGS. 5–7). Cam 112 is mounted on a cam holder 116 which is in fixed position on frame member 120.

With the construction described, and as best seen in FIGS. 3 and 7, the outer extremity of a wheel assembly, such as 72, may move against, or closely adjacent, the cylindrical outer surface of drum 54 to receive an elastic therefrom, and its associated gripper assembly may move in a space inwardly therefrom to grip an end portion of an elastic received by the transfer wheel assembly from drum 54. The frustro-conical configuration of the mechanism provides sufficient space in which the clamping mechanism may operate efficiently to grip an end of an elastic.

Each wheel assembly is mounted on a shaft 96 fixed in bearings, not shown, mounted in cam holder 116.

Figure 8:
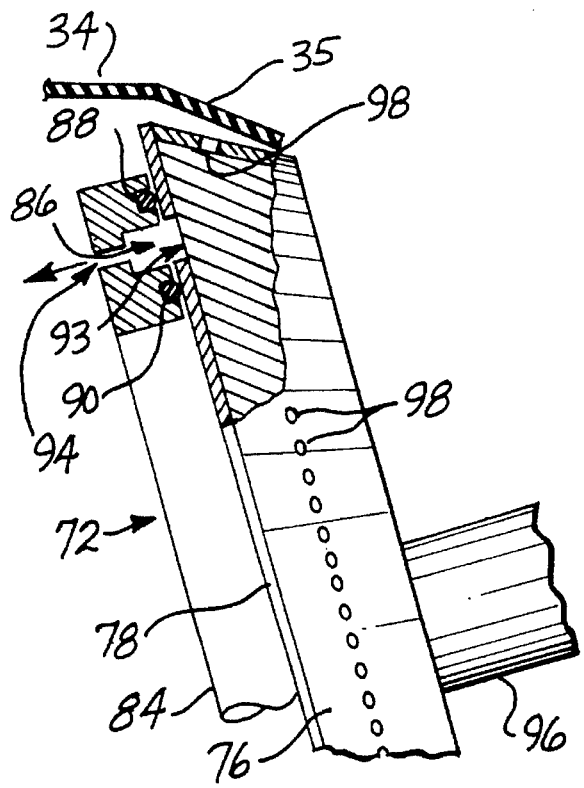
FIG. 8 shows an alternative construction of an elastic transfer wheel.
Figure 10:
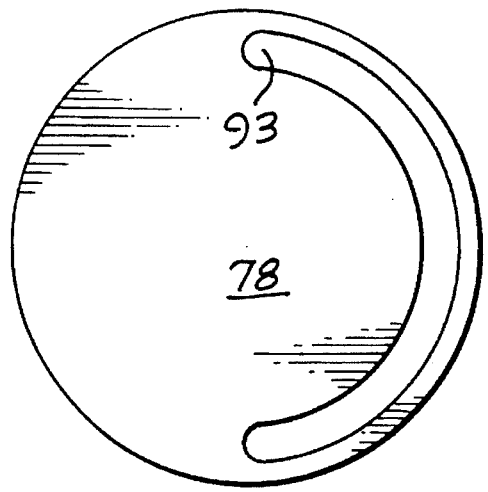
FIG. 10 shows the backing plate of the elastic transfer wheel of FIG. 8.

An alternate version of the transfer wheel is shown in FIGS. 8 and 10. Here the frustro-conical portion 76 is drilled with a series of peripheral orifices 98 in communcation with a hollow interior portion. These in turn communicate with chamber 86 in the pneumatic ring through the slot 93 in backing plate 78. This time, instead of air pressure being introduced into orifice 94, the assembly is connected to a vacuum pump. Pneumatic ring 84 is ported in backing plate 78 as seen in FIG. 10 so that the end 35 of elastic strip 34 is held to the transfer wheel by vacuum through approximately 180° of revolution.

Referring again to FIGS. 3 and 4, the method of operation of the mechanism can now be readily understood. In FIG. 3 a strip of untensioned elastic 34 has just been picked up by the two transfer wheel assemblies 70, 72 from the vacuum drum 54. These wheels are rotated by a drive mechanism, not shown at a circumferential speed which is equivalent to the linear speed of polyethylene sheet 16. In FIG. 4 the transfer wheels, or mechanisms 70, 72 have rotated 180° and are applying the now tensioned elastic strip 34 to the backing film, where it is held by fine adhesive lines 29. In this version of the invention a pressure roll assembly 122 having a shaft 124 mounted in fixed bearings 126, 128 has pressure rollers 130 which are spaced so that they normally run between the fine adhesive lines 29. As the tensioned elastic is applied to backing film 16 the rollers 130 press it firmly against the adhesive so that it is then bonded to the backing film.

Figure 2:
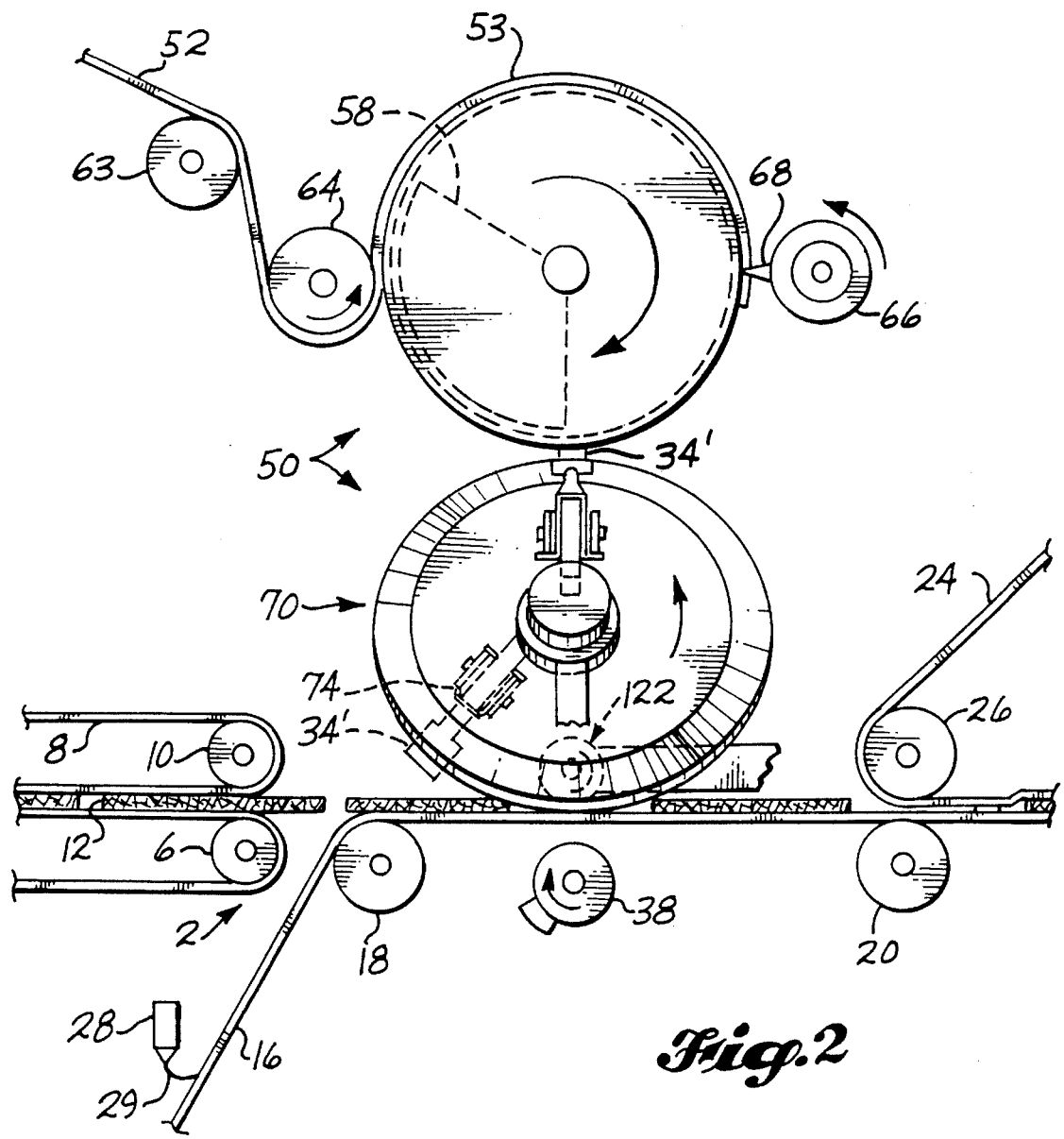
FIG. 2 shows a view similar to FIG. 1 of a somewhat different embodiment of the invention.

The version just described is pictured in FIGS. 2, 3 and 4. A somewhat different version is shown in FIG. 1, although the method of operation is very similar. Here tensioned elastic strip 34' is about to be attached to the nonwoven cover sheet 24. As this advances around reversing roll 26 it is firmly pressed into position by bump roll 38.

The elastic may be either a natural rubber sheet, such as is available from Fulflex, Inc., Middletown, R.I. or Stevens Elastomerics, Greensboro, N.C., or it may be a synthetic type such as a polyurethene-polyester cellular elastic foam, such as that available from Scotfoam, Eddystone, Pa.

Waist elastic in diapers is normally tensioned so that the applied length is about 130–140% of the untensioned length. It will be readily evident that the amount of tensioning can be controlled by adjusting the angle of inclination of the elastic transfer wheels. Some control may also be achieved by applying the elastic from the perforated drum to the transfer wheels at a point to one side or the other of the position at which they are closest together.

It will be readily understood by those skilled in the art that many variations can be made in the present invention without departing from the spirit thereof. As one example, the transfer wheels could be equipped with short spikes to hold the elastic while it is being stretched and moved from the supply drum to the point of application. The vacuum drum for transferring untensioned elastic strips to the inclined rolls may be replaced with other well known types of singulating and transfer devices. It is the intent of the inventor that any of these variations should be included within the scope of the invention insofar as they are found within the compass of the appended claims.

I claim:

1. Apparatus for applying strips of tensioned elastic material transversely to a moving sheet or web which comprises:

a pair of spaced-apart opposed rotary elastic transfer mechanisms located in mirror image relationship transversely across the moving web so as to straddle the web, said transfer mechanisms having rotational axes and distal portions spaced substantially equal distances outwardly from said axes, with the distal portions of the opposed transfer mechanisms positioned in mirror image to each other, said transfer mechanisms lying in planes which, when projected onto the plane of the web, describe lines parallel to the longitudinal axis of the web, with the axes of the transfer mechanisms being located so that the distal portions at one point of rotation are adjacent and essentially tangent to the plane of the web, said transfer mechanisms being inclined relative to each other so that the distance between their distal portions is greatest where they pass in rotation adjacent the web and is least where they are spaced the greatest distance from the web, each transfer mechanism having an outer rim surface sloping radially toward its center of rotation and away from the other transfer mechanism, supply means operable to provide an untensioned elastic strip to the transfer mechanisms adjacent the point of least distance therebetween, comprising a drum having its longitudinal axis normal to the longitudinal axis of the moving web and located so as to be in peripheral proximity to the transfer mechanisms at the point where the distance between them is least, elastic strip supply means to provide a strip of elastic to the periphery of the drum at a region spaced from the transfer mechanisms, holding means to retain the strip on the drum from the region of supply to the region of closest proximity to the transfer mechanisms and then release the strip to the transfer mechanisms, drive means for rotating the drum at a speed essentially identical to that of the circumferential speed of the transfer mechanism and the linear speed of the moving web, elastic strip retaining means associated with each transfer mechanism including clamping mechanism having a gripping portion spaced radially inwardly from the outer extremity of the distal portion of the transfer mechanism to grip a strip of elastic at the point of application and release it at the plane of the web after angular rotation of the mechanism, and drive means for the transfer mechanisms to rotate them at a circumferential speed essentially equal to the linear speed of the moving web, so that a strip of elastic is stretched and tensioned between the point of application to the transfer mechanisms and the point of release at the point of the web.

2. The apparatus of claim 1, in which the drum has a foramina surface with the foraminae in communication with an internal volume, means for connecting the internal volume to a vacuum source to hold the elastic strip to the surface, and means for breaking the vacuum adjacent the transfer mechanism to release the elastic strip to the transfer mechanism.

3. The apparatus of claim 1, in which the clamping mechanism comprises cam actuated clamps located on and fully within the radially outer extremity of surface portions of the transfer mechanism.

4. The apparatus of claim 1, in which the elastic strip retaining means on the transfer mechanism comprises foramina in the peripheral surface of the transfer mechanism with the foramina being in communication with an internal volume, means for connecting the internal volume to a vacuum source to hold the elastic strips to the transfer mechanism from the point where the strip is received from the supply means and means to break the vacuum at the point where the strip is applied to the moving web.

5. The apparatus of claim 1, wherein a transfer mechanism further comprises fluid flow means operable to draw a loose end portion of an elastic strip released from the drum toward the rim surface of the transfer mechanism to a position to be gripped by the clamping mechanism.

6. The apparatus of claim 5, wherein said fluid flow means comprises means for directing a relatively high velocity stream of fluid across said rim surface to produce a Bernoulli effect to draw an end portion of an elastic strip toward said surface.

7. The apparatus of claim 5, wherein said fluid flow means comprises an orifice opening to the rim surface and vacuum means operatively connected to said orifice to produce a reduced fluid pressure at said orifice to draw an end portion of an elastic strip toward said surface.

8. The apparatus of claim 7, wherein said vacuum means includes means operable to break said vacuum prior to the elastic strip reaching the point of release.

* * * * *